United States Patent [19]
Baba

[11] Patent Number: 6,049,743
[45] Date of Patent: Apr. 11, 2000

[54] METHOD OF DESIGNING DENTAL PROSTHESIS MODEL AND COMPUTER PROGRAM PRODUCT THEREFOR

[75] Inventor: Masami Baba, Konan-machi, Japan

[73] Assignee: Technology Research Association of Medical and Welfare Appartus, Tokyo, Japan

[21] Appl. No.: 08/924,885

[22] Filed: Sep. 5, 1997

[51] Int. Cl.$^7$ .................................................. G06F 19/00
[52] U.S. Cl. ........................................... 700/163; 433/172
[58] Field of Search ...................... 364/474.24, 474.25, 364/474.05, 474.15; 433/214, 34

[56] References Cited

U.S. PATENT DOCUMENTS

| | | | |
|---|---|---|---|
| 4,611,288 | 9/1986 | Duret et al. | 364/474.05 |
| 4,663,720 | 5/1987 | Duret et al. | 364/474.05 |
| 4,742,464 | 5/1988 | Duret et al. | 364/474.25 |
| 5,224,049 | 6/1993 | Mushabac | 364/474.05 |
| 5,527,182 | 6/1996 | Willoughby | 433/172 |

FOREIGN PATENT DOCUMENTS 2-52964 of 1983 Japan .

OTHER PUBLICATIONS

Y. Shomura et al., "Three–Dimensional Measurement of Tooth Shape (Report 4)—Measurement of Z–Direction Movement with Laser Displacement Gauge", published in 'Dental Materials and Appliances, vol. 8, Special Issue 14 (1989).

New Common Dental Dictionary, published by Medical–Dental–Pharmaceutical Publishing House, pp. 127–128.

*Primary Examiner*—William Grant
*Assistant Examiner*—Chad Rapp
*Attorney, Agent, or Firm*—Foley & Lardner

[57] ABSTRACT

A method of designing a dental prosthesis model, such as a bridge or a crown. The method includes measuring a three-dimensional configuration of a dentition of a subject in order to obtain configuration data of upper and lower jaw dentitions of a subject. The dentition configuration data is stored. Also stored is pontic model data defining standard pontic model configurations corresponding to the configurations of individual teeth. The pontic model is expressed as a combination of patches that are stored as configuration expression data, and morphology definition data indicating a characteristic morphology of the teeth of the pontic model. The pontic model data is read out, corresponding to a tooth or teeth where the dental prosthesis is to be placed. Based on the read-out pontic model data, crown model data indicating a crown region is made. The crown model data is displayed so that it can be superimposed on a dentition configuration diagram. The crown model is then deformed, by modifying the patches, for example, to form a desired gap with respect to formation of the dental prosthesis.

19 Claims, 10 Drawing Sheets

METHOD OF DESIGNING DENTAL PROSTHESIS MODEL AND COMPUTER PROGRAM PRODUCT THEREFOR

BACKGROUND OF THE INVENTION

1. Field of the Invention

The present invention relates to a method of designing a dental prosthesis model of crown, bridge, or the like by using a computer; and a computer program product storing a program for executing this method.

2. Related Background Art

A dental prosthesis such as crown, bridge, or the like has been made by a process in which a dentist takes an impression of abutment teeth and their surrounding teeth and, based on it, a dental technician makes the dental prosthesis. The conventional method mainly comprises manual operations, thus requiring much labor and time for designing and making the dental prosthesis.

Accordingly, there has been proposed and being realized a method in which configurations of abutment teeth, their adjacent and pairing teeth, and the like are fed into a computer, a dental prosthesis model conforming thereto is made on the computer, and a dental prosthesis is machined on the basis of thus made model, i.e., method of making a dental prosthesis by means of CAD/CAM (computer aided design/computer aided manufacture) technique. Specifically, there has been SOPHA system of Sopha (France) using a technique in which a crown model is expressed and designed on a computer and is stored in a database.

Nevertheless, a dental prosthesis is used not only for crowns but also for bridges and the like. In order to design all kinds of dental prostheses on a computer (by means of CAD/CAM technique), it is necessary to design all kinds of dental prosthesis models for crowns, pontics, bridges, and the like. In this case, according to the conventional method, it is necessary for each of the crowns, pontics, and bridges to be designed on the computer and be arranged in a database, thereby requiring a very large database. Accordingly, the labor of management increases, thus making it difficult to achieve efficient designing.

SUMMARY OF THE INVENTION

In view of the foregoing, it is an object of the present invention to provide a designing method which can design various kinds of dental prostheses easily and efficiently by using a computer, and a computer program product therefor.

In the present invention, in the case where a dental prosthesis model to be attached to a part of upper and lower jaw dentitions which is needed to be restored is designed on a computer, pontic model data each of which corresponds to a configuration of each tooth are made and stored in a database, and these pontic model data are used to design a dental prosthesis model of crown, bridge, or the like.

Namely, a first method of designing a dental prosthesis model in accordance with the present invention is a method of designing, by means of a computer, a dental prosthesis model to be attached to a part of upper and lower jaw dentitions which is to be restored, the method comprising the steps of:

displaying a dentition configuration diagram resulting from an image conversion of dentition configuration data obtained by measurement of a three-dimensional configuration of upper and lower jaw dentitions of a subject;

reading out, from a database containing pontic model data respectively indicating standard pontic models which correspond to configurations of individual teeth, pontic model data corresponding to a tooth of the above-mentioned part;

making, based on the read-out pontic model data, crown model data indicating a crown region;

displaying a crown model resulting from an image conversion of the crown model data so that the crown model is superimposed on the dentition configuration diagram; and deforming the crown model so that the crown model forms a desired gap with respect to pairing and adjacent teeth and a gum without interfering therewith.

A second method of designing a dental prosthesis model in accordance with the present invention is a method of designing, by means of a computer, dental prosthesis models to be attached to a plurality of parts of upper and lower jaw dentitions which are to be restored, the method comprising the steps of:

displaying a dentition configuration diagram resulting from an image conversion of dentition configuration data obtained by measurement of a three-dimensional configuration of upper and lower jaw dentitions of a subject;

reading out, from a database containing pontic model data respectively indicating standard pontic models which correspond to configurations of individual teeth, pontic model data respectively corresponding to teeth of the plurality of parts;

making, based on at least one piece of pontic model data in the read-out pontic model data, crown model data indicating a crown region;

displaying a crown model and a pontic model respectively resulting from image conversions of the crown model data and remaining pontic model data so that the crown model and pontic model are superimposed on the dentition configuration diagram;

deforming each of the crown and pontic models so that each of the crown and pontic models forms a desired gap with respect to pairing and adjacent teeth and a gum without interfering therewith; and making a bridge model by connecting the crown and pontic models to each other.

In each method of the present invention mentioned above, a dental prosthesis model of crown, bridge, or the like is designed solely on the basis of prepared pontic model data indicating standard pontic models corresponding to configurations of individual teeth. Accordingly, in the method of the present invention, as a database, only data concerning standard pontic models corresponding to the configurations of individual teeth are necessary. Namely, data to be prepared and stored beforehand are only standard pontic model data concerning 8 teeth each on the right and left sides of the upper and lower jaws, i.e., standard pontic model data of at least 32 teeth. Consequently, in accordance with the method of the present invention, the database can be made smaller than that conventionally used and can become easy to manage, whereby a dental prosthesis model of crown, bridge, or the like can be designed efficiently.

A first computer program product for designing a dental prosthesis model in accordance with the present invention is a computer program product, to be used in conjunction with a computer, for designing a dental prosthesis model, the computer comprising a storage device for storing a database containing pontic model data respectively indicating standard pontic models corresponding to configurations of individual teeth, an input device, a display device, and a reading device for reading out information from a medium which is usable by the computer; the product comprising:

a dental prosthesis model designing program, which is readable by the computer and materialized in the medium, for designing by means of the computer, based on the pontic model data, a dental prosthesis model to be attached to a part in upper and lower jaw dentitions which is to be restored;

the dental prosthesis model designing program comprising:

a dentition configuration diagram displaying program for displaying, on the display device, a dentition configuration diagram resulting from an image conversion of dentition configuration data obtained by measurement of a three-dimensional configuration of upper and lower jaw dentitions of a subject;

a pontic model data reading program for reading out, from the database, pontic model data corresponding to a tooth of the above-mentioned part;

a crown model data making program for making, based on the read-out pontic model data, crown model data indicating a crown region;

a superimposition displaying program for displaying a crown model resulting from an image conversion of the crown model data so that the crown model is superimposed on the dentition configuration diagram; and a model deforming program for deforming the crown model so that the crown model forms a desired gap with respect to pairing and adjacent teeth and a gum without interfering therewith.

A second computer program product for designing a dental prosthesis model in accordance with the present invention is a computer program product, to be used in conjunction with a computer, for designing a dental prosthesis model, the computer comprising a storage device for storing a database containing pontic model data respectively indicating standard pontic models corresponding to configurations of individual teeth, an input device, a display device, and a reading device for reading out information from a medium which is usable by the computer; the product comprising:

a dental prosthesis model designing program, which is readable by the computer and materialized in the medium, for designing by means of the computer, based on the pontic model data, dental prosthesis models to be attached to a plurality of parts in upper and lower jaw dentitions which are to be restored;

the dental prosthesis model designing program comprising:

a dentition configuration diagram displaying program for displaying, on the display device, a dentition configuration diagram resulting from an image conversion of dentition configuration data obtained by measurement of a three-dimensional configuration of upper and lower jaw dentitions of a subject;

a pontic model data reading program for reading out, from the database, pontic model data respectively corresponding to teeth of the plurality of parts;

a crown model data making program for making, based on at least one piece of pontic model data in the read-out pontic model data, crown model data indicating a crown region;

a superimposition displaying program for displaying a crown model and a pontic model respectively resulting from image conversions of the crown model data and remaining pontic model data so that the crown model and pontic model are superimposed on the dentition configuration diagram;

a model deforming program for deforming each of the crown and pontic models so that each of the crown and pontic models forms a desired gap with respect to pairing and adjacent teeth and a gum without interfering therewith; and a model connecting program for connecting the crown and pontic models to each other so as to make a bridge model.

In a method conforming to the dental prosthesis model designing program stored in the computer program product in accordance with the present invention, a dental prosthesis model of crown, bridge, or the like is designed solely based on prepared pontic model data indicating standard pontic models corresponding to configurations of individual teeth. Accordingly, in the method conforming to the dental prosthesis model designing program in accordance with the present invention, as a database, only data concerning standard pontic models corresponding to the configurations of individual teeth are necessary. Namely, data to be prepared and stored beforehand are only standard pontic model data concerning 8 teeth each on the right and left sides of the upper and lower jaws, i.e., standard pontic model data of at least 32 teeth. Consequently, when the dental prosthesis model designing program in accordance with the present invention is used, the database can be made smaller than that conventionally used and can become easy to manage, whereby a dental prosthesis model of crown, bridge, or the like can be designed efficiently.

Preferably, the pontic model in accordance with the present invention includes a characteristic morphology (e.g., cuspid apex, groove and ridge positioned within an occlusal surface, marginal ridge, height of contour, and margin line corresponding to a gum line) of a tooth corresponding to the pontic model and is formed by a plurality of three-dimensional curved patches combined together. In this case, the pontic model data include morphology definition data which indicate the characteristic morphology of the tooth corresponding to the pontic model, and configuration expression data which indicate a three-dimensional configuration and constitutional position of each patch and are changeable upon alteration of the morphology definition data. The pontic model data are preferably expressed by a combination of these morphology definition data and configuration expression data. Accordingly, in the step (model deforming program) of deforming the above-mentioned model (crown model and/or pontic model), the configuration of the model can be deformed easily and securely by simply moving a point corresponding to the characteristic morphology on a screen, whereby the designing of a dental prosthesis model of crown, bridge, or the like becomes easier.

Preferably, the pontic model data in accordance with the present invention include deforming region definition data indicating a plurality of deforming regions divided by an interface passing through a groove of an occlusal surface in the pontic model and extending from the groove to a base surface of the pontic model. In this case, in the step (model deforming program) of deforming the above-mentioned model (crown model and/or pontic model), the model can be deformed more easily and accurately by using the deforming region as a unit, whereby the designing of a dental prosthesis model of crown, bridge, or the like becomes easier.

Preferably, the pontic model data in accordance with the present invention further include margin line data indicating a margin line corresponding to a gum line in the pontic model. In this case, in the step (crown model data making program) of making the crown model data, it is possible to efficiently and securely make crown model data indicating the crown region resulting from elimination, based on the margin line data, of a base region to be embedded in the gum from the pontic model. Accordingly, the designing of a dental prosthesis model of crown, bridge, or the like becomes easier.

Here, "pontic model" refers to a model of an artificial tooth to fill an intermediate position (i.e., position corresponding to a lost tooth without an abutment tooth) of a bridge, and is typically constituted by a crown region having an occlusal surface on one side and a base region, connected to the other side of the crown region, to be embedded in a gum. Such a pontic model is disclosed, for example, in New Common Dental Dictionary, published by Medical-Dental-Pharmaceutical Publishing House, p. 127, which is incorporated herein by reference.

On the other hand, "crown model" refers to a model of a dental prosthesis (artificial crown) to be mounted on a broken tooth (abutment tooth), whereas "bridge model" refers to a model of an artificial bridge in which at least one pontic model and at least one crown model are connected to each other.

A method of obtaining three-dimensional data by three-dimensionally measuring such a tooth model is disclosed, for example, in Y. Somura et al., "Three Dimensional Measuring of Tooth Configuration (The Fourth Report) -Measuring of Z-Direction Movement of Laser Displacement Meter-", Dental Materials and Tools, 8 (Special Issue 14): p. 124–125 (1989) and K. Terada et al., "Measuring of Tooth Configuration and Modeling for Computer", Medical Electronics and Biological Engineering, 27 (Autumn Special Issue): p. 207 (1989), which are incorporated herein by reference.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1:
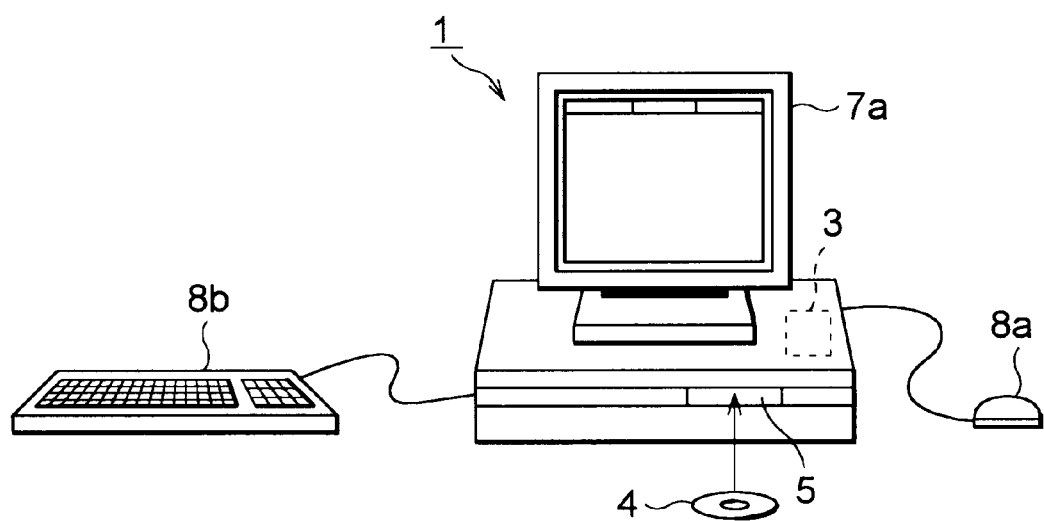
FIG. 1 is a perspective view showing an example of a computer system performing the method of designing a dental prosthesis model in accordance with the present invention.
Figure 2:
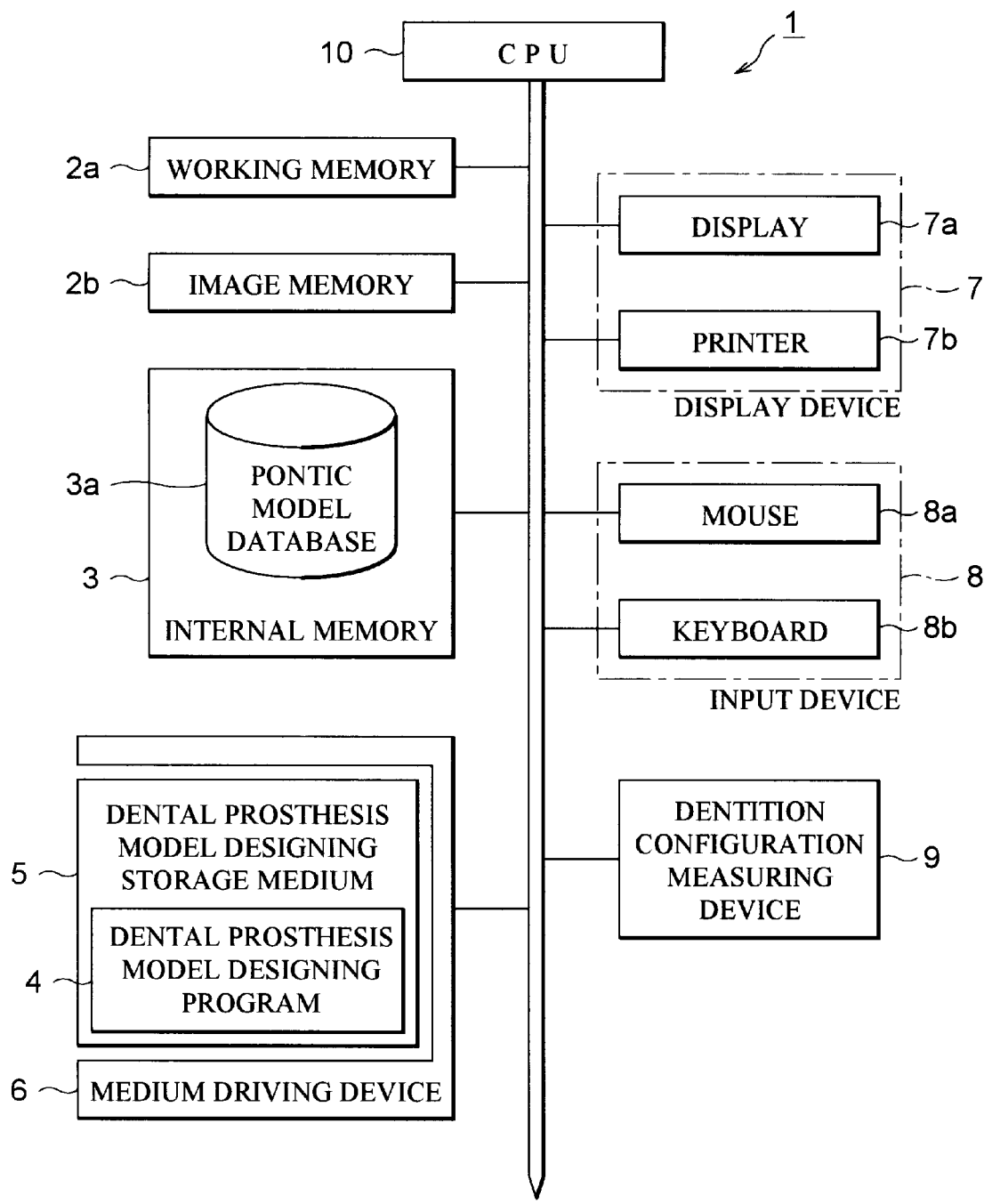
FIG. 2 is a block diagram showing a configuration of an example of the computer system performing the method of designing a dental prosthesis model in accordance with the present invention.
Figure 3:
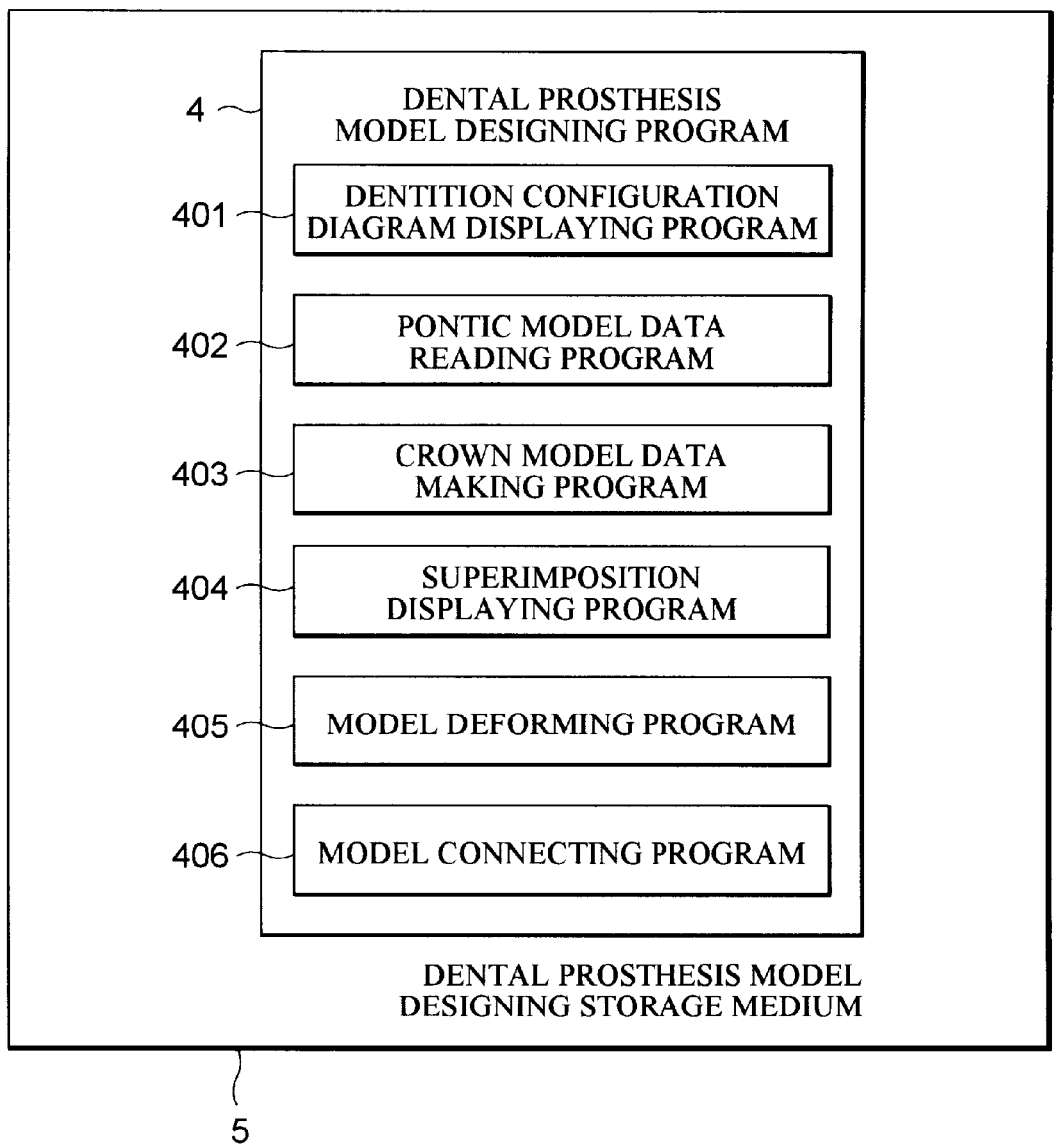
FIG. 3 is a block diagram showing a configuration of an example of a storage medium (computer program product) for designing a dental prosthesis model in accordance with the present invention.

In the following, preferred embodiments of the present invention will be explained with reference to the accompanying drawings. FIG. 1 is a perspective view showing an example of a computer system performing the method of designing a dental prosthesis model in accordance with the present invention; FIG. 2 is a block diagram showing the configuration of this computer system in detail; and FIG. 3 is a block diagram showing, in detail, a storage medium (computer program product) for designing a dental prosthesis model shown in FIG. 2.

The computer system 1 for designing a dental prosthesis model in accordance with the present invention comprises a working memory 2a for temporarily storing data; an image memory 2b for storing image data; an internal memory 3 storing a pontic model database 3a which will be explained later; a medium driving device 6 which can accommodate and drive a dental prosthesis model designing storage medium (computer program product) 5 storing a dental prosthesis model designing program 4 which will be explained later; a display device 7 constituted by a display 7a and a printer 7b; an input device 8 constituted by a mouse 8a and a keyboard 8b; a dentition configuration measuring device 9; and a CPU 10 for controlling execution of the dental prosthesis model designing program 4 and the like.

The dental prosthesis model designing program 4 comprises:

(i) a dentition configuration diagram displaying program 401 for displaying, on the display device 7, a dentition configuration diagram resulting from an image conversion of dentition configuration data obtained when a three-dimensional configuration of upper and lower jaw dentitions of a subject is measured by means of the dentition configuration measuring device 9;

(ii) a pontic model data reading program 402 for reading out, from the database 3a, pontic model data corresponding to a tooth of a part to be restored;

(iii) a crown model data making program 403 for making, based on at least one piece of pontic model data in the read-out pontic model data, crown model data indicating a crown region;

(iv) a superimposition displaying program 404 for displaying, on the display device 7, a crown model and a pontic model respectively resulting from image conversions of the crown model data and remaining pontic model data so that the crown model and pontic model are superimposed on the dentition configuration diagram;

(v) a model deforming program 405 for deforming each of the crown and pontic models so that each of the crown and pontic models forms a desired gap with respect to pairing and adjacent teeth and a gum without interfering therewith; and (vi) a model connecting program 406 for connecting the crown and pontic models to each other so as to make a bridge model. Specific contents of processings in the above-mentioned programs will be explained later.

Here, for designing, changing, displaying, and the like of three-dimensional data in the dental prosthesis model designing program 4, a CAD program or the like is used. Specifically, UNIX is used as its OS, and X-Window and PEX library (three-dimensional display drawing library) are used for drawing.

As the recording medium 5, a disk-shaped recording medium such as flexible disk or CD-ROM as well as a tape type recording medium such as magnetic tape may be used, for example. According to the recording medium 5, a flexible disk drive unit, a CD-ROM drive unit, a magnetic tape drive unit, or the like is used as the medium driving device 6.

The dentition configuration measuring device 9 is a three-dimensional measuring instrument which measures a three-dimensional configuration of a dentition or residual ridge of a subject so as to obtain dentition configuration data as three-dimensional coordinate data, and stores thus obtained dentition configuration data into the working memory 2a. Such dentition configuration measuring device 9 may be either of a contact type or of a non-contact type such as, for example, Tristation (trade name) available from Nikon Corp.

Figure 4A:
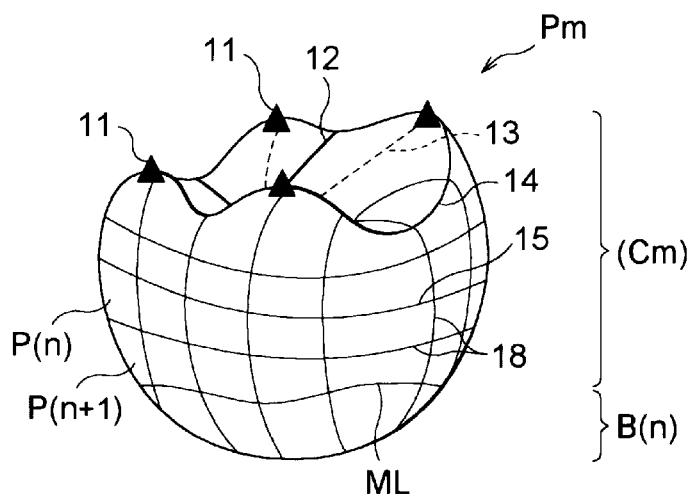
FIGS. 4A and 4B are respectively a schematic perspective view and a schematic top plan view, both showing an example of a pontic model in accordance with the present invention.
Figure 4B:
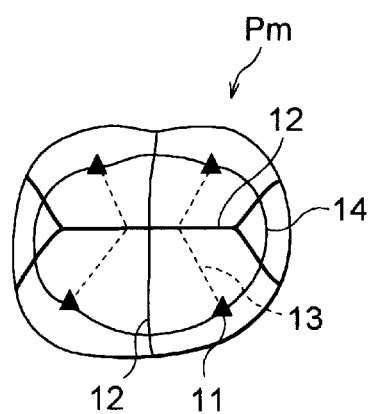

In the internal memory 3, the database 3a containing pontic model data defining standard pontic model configurations corresponding to the configurations of individual teeth is constructed. A pontic model $P_m$ stored in this database 3a is, for example, as shown in FIGS. 4A and 4B, expressed by a combination of patches $(P_{(1)}, P_{(2)}, \ldots, P_{(n)}, P_{(n+1)}, \ldots)$ dividing the model into a number of rectangular curved surfaces. Data indicating the three-dimensional curved surface configuration of each patch $P_{(n)}$ and the constitutional position (three-dimensional position) of each patch are stored in the database 3a as configuration expression data.

Though it is possible for such configuration expression data by themselves to express the outer configuration of the pontic model $P_m$ such as that shown in FIGS. 4A and 4B, the model is hard to deform and process on the computer 1 in this case. Accordingly, the database 3a also stores morphology definition data indicating a characteristic morphology of the tooth in the pontic model. The morphology definition data include cuspid apexes 11, grooves 12 and ridges 13 which are positioned within an occlusal surface, a marginal ridge 14, a height of contour 15, a margin line ML, and the like, thereby defining the characteristic morphology of the pontic model $P_m$. Also, the morphology definition data include auxiliary lines 18 defining each patch $P_{(n)}$, thereby clearly defining each patch $P_{(n)}$ together with the above-mentioned characteristic morphology.

Figure 5:
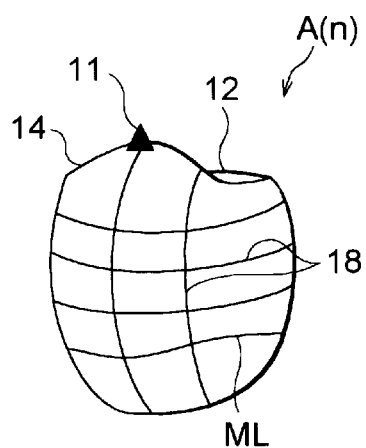
FIG. 5 is a schematic perspective view showing one deforming region in the pontic model shown in FIG. 4A.

The morphology definition data also include data defining a plurality of deforming regions $A_{(n)}$ which are obtained when the grooves 12 in the occlusal surface in the pontic model $P_m$ are extended in the base surface direction (i.e., substantially vertically) so as to divide the pontic model $P_m$. FIG. 5 shows an example of such a deforming region $A_{(n)}$ which includes a plurality of patches positioned within the region separated by the groove 12 vertically extended downward. As will be explained later, this deforming region $A_{(n)}$ is a region used when the tooth configuration is deformed on the computer 1, and the deformation is performed while using each deforming region $A_{(n)}$ as a unit. Accordingly, though the patches smoothly connect with each other within each deforming region $A_{(n)}$, they do not necessarily connect with each other smoothly at boundaries between the individual deforming regions.

Figure 6A:
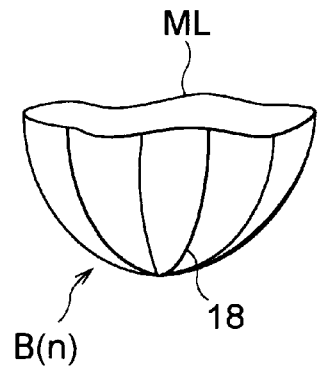
FIGS. 6A, 6B, and 6C are schematic perspective views respectively showing various examples of a base region in the pontic model in accordance with the present invention.
Figure 6B:
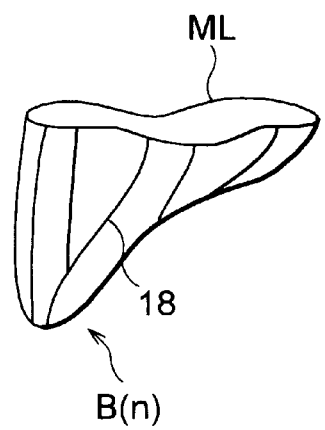
Figure 6C:
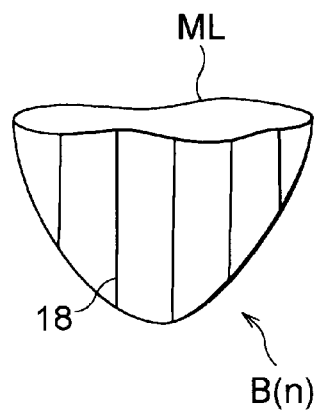

The morphology definition data further include data defining a base region $B_{(n)}$ located below the margin line ML in the pontic model $P_m$. FIGS. 6A, 6B, and 6C respectively show examples of the base region $B_{(n)}$. As can be seen from these drawings, in conformity with individual teeth, such forms as those of separated bottom type, ship bottom type (FIG. 6A), lopsided type (FIGS. 6B and 6C), and the like are set for each pontic model. Here, the auxiliary lines 18 defining the patches in the base region are arbitrarily set as lines converging onto the base surface, lines naturally extending downward, and the like.

Thus, 8 pieces each on the right and left sides of the upper and lower jaws (32 pieces in total) of pontic model data expressed by the configuration expression data and morphology definition data recorded in the database 3a are set so as to correspond to the configurations of the individual teeth.

Figure 7:
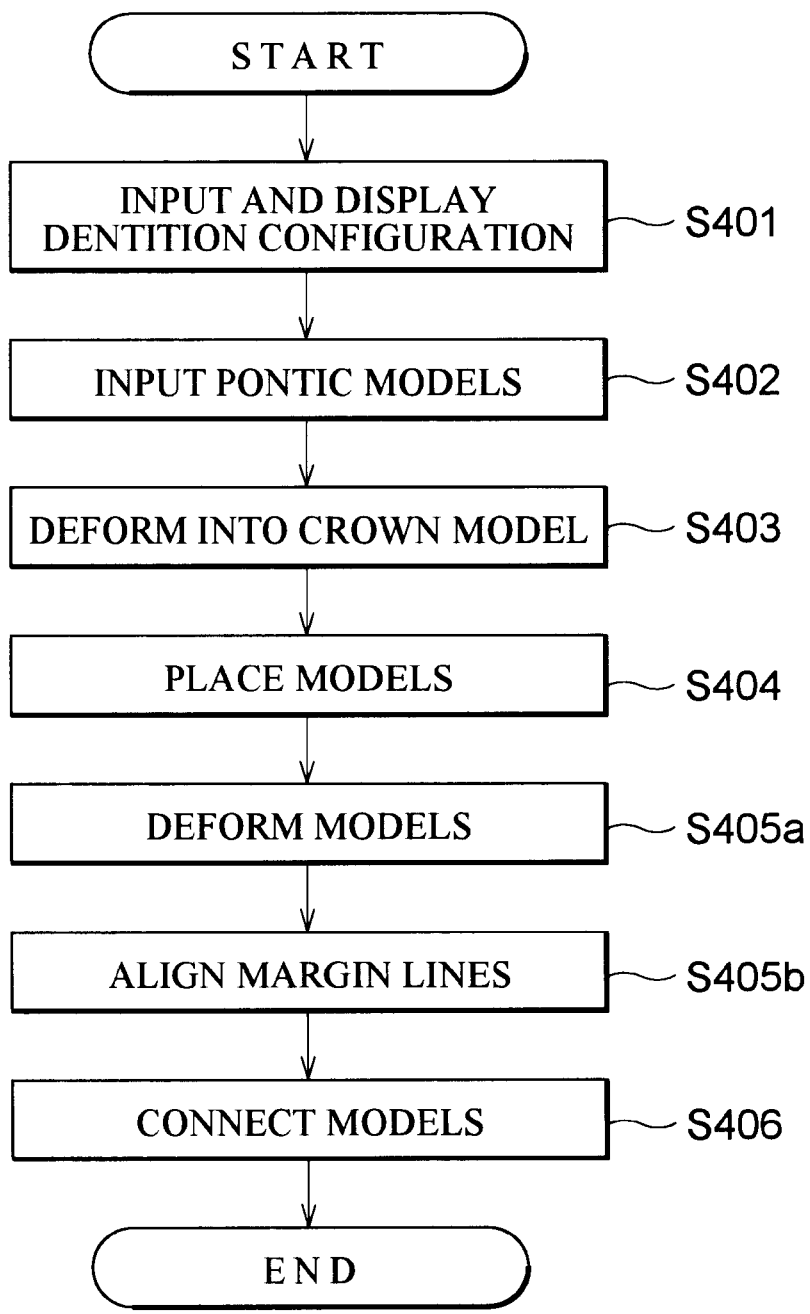
FIG. 7 is a flowchart showing an example of a dental prosthesis model designing program in accordance with the present invention for performing the method of the present invention.

In the following, a method of designing a bridge model, according to the dental prosthesis model designing program 4 stored in the recording medium 5, by means of the pontic model data thus stored in the database 3a will be explained. This method is executed according to the flowchart shown in FIG. 7.

Figure 8A:
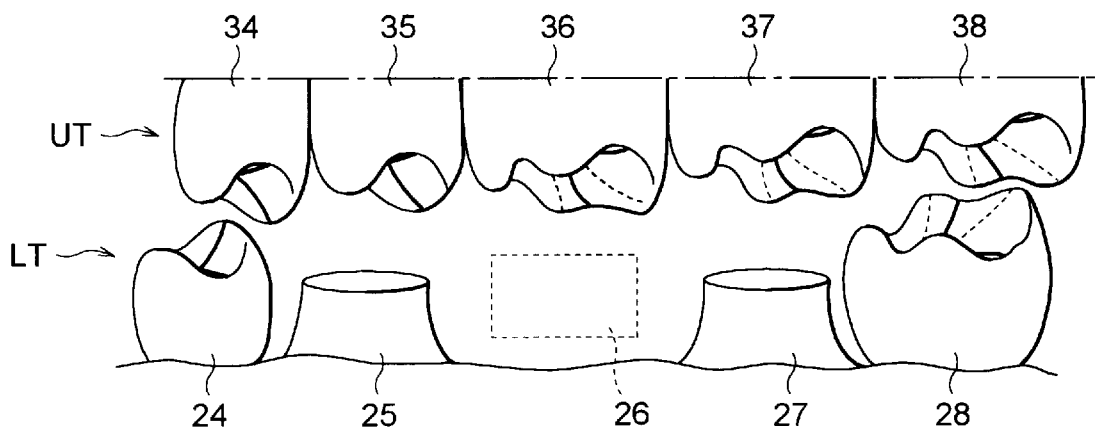
FIGS. 8A and 8B are respectively a schematic perspective view showing an example of upper and lower jaw dentitions represented on a display in a dentition configuration displaying step and a schematic perspective view showing an example of a bridge to be attached thereto.
Figure 8A:
Figure 8B:
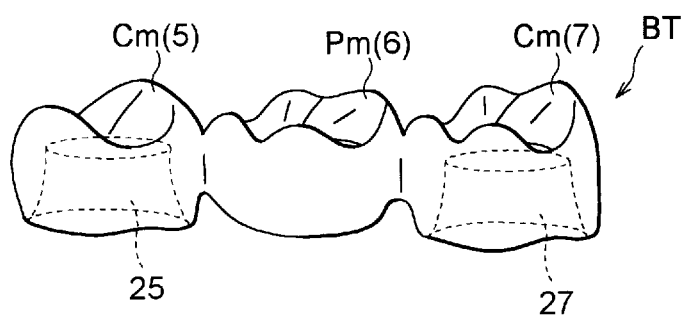

First, the dentition configuration displaying program 401 is invoked, whereby a dentition configuration is inputted and displayed as follows. Namely, first, gypsum casts of dentitions of upper and lower jaws in a basic state of a subject to whom a bridge is to be attached are taken, and three-dimensional measurement of these casts is performed by means of the dentition configuration measuring device 9 in a state where the gypsum casts are held without altering the original positional relationship between the upper and lower jaws. From the resulting image data, dentition three-dimensional configuration data are obtained, and thus obtained data are read into the CAD system in the computer 1 so as to be represented on the display 7a (step S401). In this measurement, configurations of teeth surrounding the teeth to which the bridge is attached, i.e., fourth to eighth teeth in the upper and lower jaw dentitions, are measured and, as shown in FIG. 8A, are represented on the display 7a. As can be seen from this drawing, the sixth tooth 26 in the lower jaw LT is lost, and a bridge BT shown in FIG. 8B is designed so as to be attached thereto by using the fifth and seventh teeth 25 and 27 as its abutment teeth.

Subsequently, the pontic data reading program 402 is invoked, so that pontic model data corresponding to the tooth (i.e., those corresponding to the fifth to seventh teeth in the lower jaw) $P_{m(5)}$, $P_{m(6)}$, and $P_{m(7)}$ are fed into the CAD system from the database 3a (step S402). Here, the pontic model $P_{m(6)}$ is used as it is in this part since the sixth tooth 26 is lost, whereas the pontic models $P_{m(5)}$ and $P_{m(7)}$ for the fifth and seventh teeth are respectively attached to the abutment teeth 25 and 27. Accordingly, the crown model data making program 403 is invoked, and the pontic model data $P_{m(5)}$ and $P_{m(7)}$ corresponding the fifth and seventh teeth 25 and 27 are deformed into crown model data $C_{m(5)}$ and $C_{m(7)}$ (step S403). This deformation is effected by eliminating the base region $B_{(n)}$ below the margin line ML in each of the pontic models $P_{m(5)}$ and $P_{m(7)}$. Here, since the morphology definition data defining a pontic model include data defining the base region $B_{(n)}$, this region is eliminated on the display screen, so as to make the crown models $C_{m(5)}$ and $C_{m(7)}$ as shown in FIG. 9.

Figure 9:
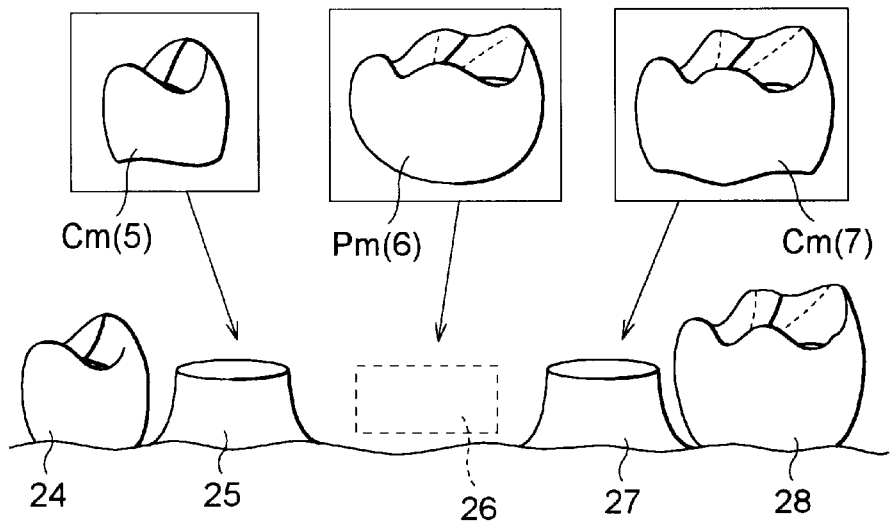
FIG. 9 is a schematic perspective view showing an example of pontic and crown models and a dentition to which they are attached.

Then, superimposition displaying program 404 is invoked, whereby thus formed crown models $C_{m(5)}$ and $C_{m(7)}$ and pontic model $P_{m(6)}$ are moved, as indicated by arrows in FIG. 9, so as to be placed at their predetermined positions (step S404). Namely, the crown models $C_{m(5)}$ and $C_{m(7)}$ are respectively placed on the abutment teeth 25 and 27, whereas the pontic model $P_{m(6)}$ is placed at the lost part 26.

Figure 10:
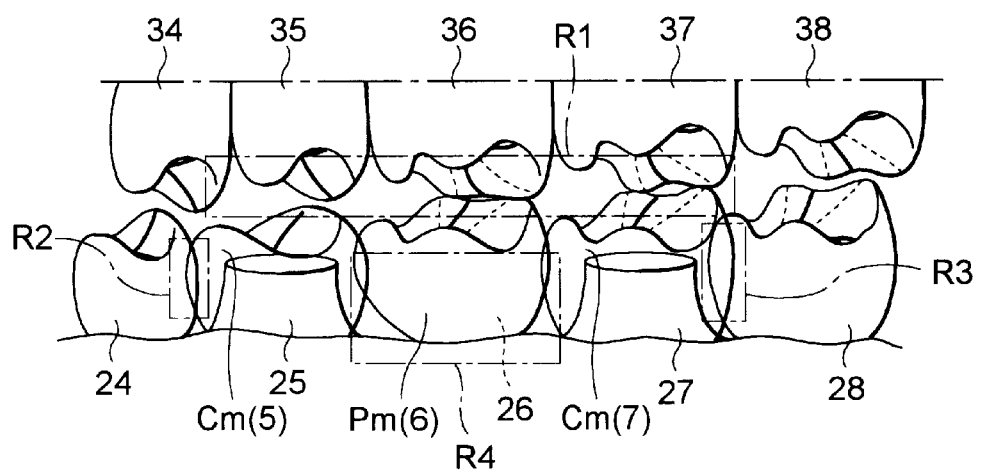
FIG. 10 is a schematic perspective view showing an example, represented on a display in a superimposition displaying step, of upper and lower jaw dentitions to which pontic and crown models are attached.

FIG. 10 shows a state where the crown models $C_{m(5)}$ and $C_{m(7)}$ and the pontic model $P_{m(6)}$ are placed at their predetermined positions. In this state, the model deforming program 405 is invoked, whereby checking of interference between these models and their pairing teeth 35, 36, and 37 (interference check at depicted region $R_1$), interference between these models and their adjacent teeth 24 and 28 (interference check at depicted regions $R_2$ and $R_3$), and interference between the pontic base portion and the gum (interference check at depicted region $R_4$) are effected, and each model is deformed such that these interferences are eliminated, while gaps therebetween become appropriate values (step S405a).

Figure 11:
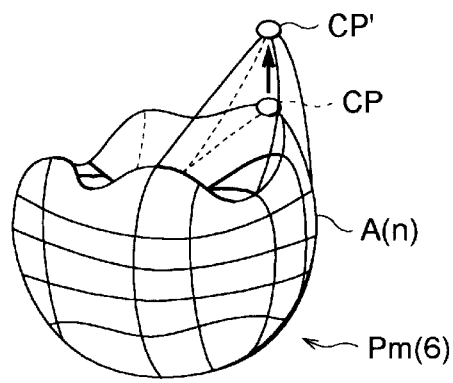
FIG. 11 is a schematic perspective view showing the states before and after a pontic model is deformed in a model deforming step.

As shown in FIG. 11, for example, this model deforming operation is effected such that the center position CP of a part requiring a deformation in the pontic model $P_{m(8)}$ is clicked with the mouse 8a and dragged to a desired position CP'. When a predetermined position is thus moved by dragging in the CAD program used for this designing process, not only the position indicating a model configuration is directly moved, but also the configuration around this point is smoothly deformed as being pulled by the movement of the point CP as shown in FIG. 11. In this case, the deformation is effected only within the deforming region $A_{(n)}$ including the point CP, without extending to its adjacent regions. Also, the amount of deformation is weighed so as to become smaller as the deformed part is farther from the point CP, thereby yielding a smooth deformation as depicted.

Figure 12:
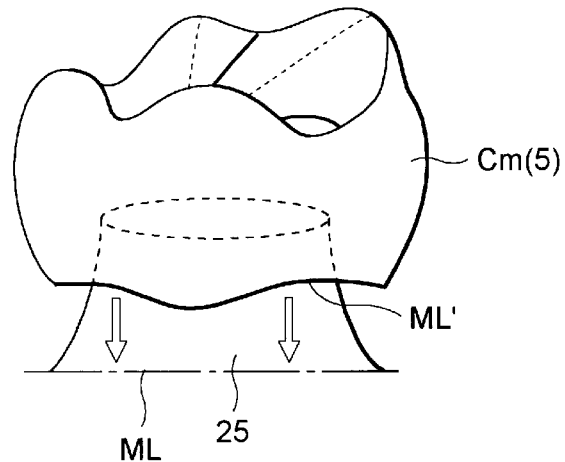
FIG. 12 is a schematic perspective view showing an example of a state, represented on a display in the superimposition displaying step, in which a crown model is attached to an abutment tooth.

Then, the margin lines ML' of the crown models $C_{m(5)}$ and $C_{m(7)}$ are aligned with the margin lines ML of their corresponding abutment teeth 25 and 27 as shown in FIG. 12, thereby substituting the margin lines ML' of the crown models for the margin lines ML of the abutment teeth 25 and 27 (step S405b). Consequently, both crown models are accurately attached to their corresponding abutment teeth 25 and 27, whereby the configuration data defining spatial configurations into which the abutment teeth 25 and 27 are inserted are set within the crown models, thus allowing a complete crown solid model to be finished.

Figure 13:
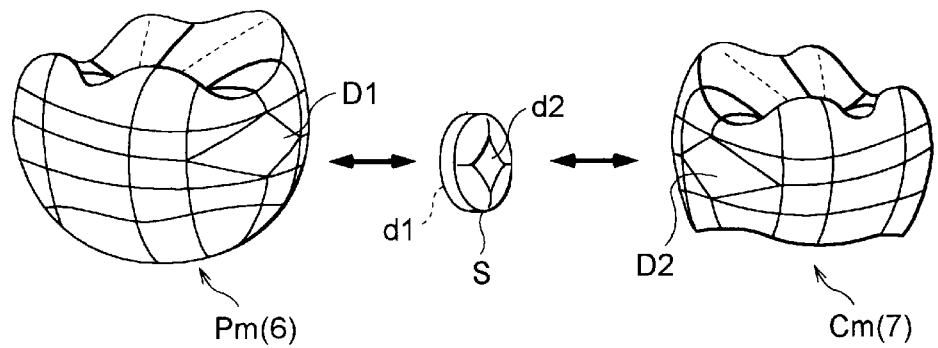
FIG. 13 is a schematic perspective view showing a state in which pontic and crown models are connected to each other in a model connecting step.

Thus accomplished is a model in a state where the pontic model $P_{m(6)}$ is inserted between the crown models $C_{(5)}$ and $C_{m(7)}$. In this state, the model connecting program 406 is invoked so as to connect these models together, whereby a model of the bridge BT is completed (step S406). This connection is established, for example, as shown in FIG. 13, by smoothly connecting the opposing faces of the pontic model $P_{m(6)}$ and crown model $C_{m(7)}$ to each other. Such a connection is effected by an operation for filling the gap between the opposing faces. For this purpose, rhombus-shaped openings $D_1$ and $D_2$ such as those depicted are respectively formed in the opposing faces of these models, and a thin plate-like connecting member S having joints $d_1$ and $d_2$ matching these openings is disposed so as to smoothly connect both models to each other.

As explained in the foregoing, by performing the procedure of steps S401 to S406, the model of the bridge BT such as that shown in FIG. 8B can be designed on the computer. Accordingly, when machining or the like is effected with this bridge model, a bridge can be manufactured easily. In the above-mentioned procedure, the order of the steps S405a and S406b is arbitrarily changeable without being restricted to that mentioned above.

Though a preferred embodiment of the present invention is explained in the foregoing, the present invention should not be restricted to the above-mentioned embodiment.

Namely, though a bridge model is designed in the above-mentioned embodiment, a crown model may be made alone in a similar process. In this case, it is unnecessary to perform the above-mentioned step S406 (model connection).

While data indicating the pontic model configurations corresponding to the configurations of the individual teeth are stored as the database 3a in the present invention, in the case where a crown model is made in the procedure of the above-mentioned step S403, data of this model may be directly stored as the crown model data and utilized for making the next bridge. Also, a base surface may be attached to a previously-made crown model so as to be used as a pontic model.

Figure 14:
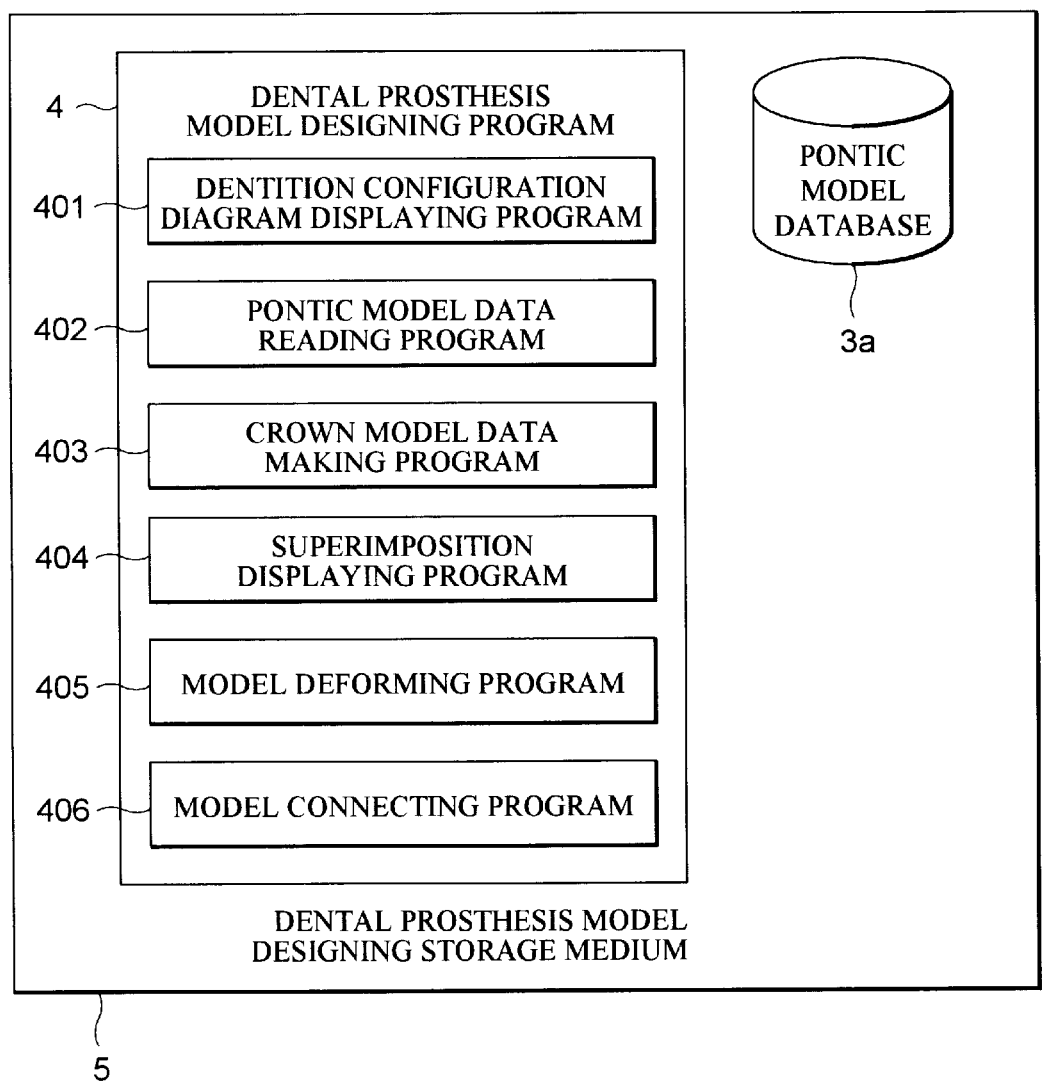
FIG. 14 is a block diagram showing a configuration of another example of the storage medium (computer program product) for designing a dental prosthesis model in accordance with the present invention.

Though the pontic model database 3a is stored in the internal memory 3 in the above-mentioned embodiment, it may also be stored in the storage medium 5 as shown in FIG. 14. On the other hand, the dental prosthesis model designing program 4 may be stored in the internal memory 3.

Also, though the above-mentioned embodiment employs UNIX as its OS (operating system), and X-Window and PEX library (three-dimensional display drawing library) for drawing, the present invention should not be restricted thereto and may use other kinds of software.

Further, though gypsum casts are used for measuring dentition configurations in the foregoing embodiment, without being restricted thereto, the dentition configurations may also be measured directly.

As explained in the foregoing, in accordance with the present invention, in order to design a dental prosthesis model on a computer, pontic models corresponding to the configurations of individual teeth are made and stored in a database, and these pontic models are used for designing dental prosthesis models of crown, bridge, and the like. Accordingly, as a database, only data indicating a pontic configuration of each tooth are necessary, whereby the database can be made smaller, its management becomes easier, and the designing can be effected efficiently.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 236249/1996 filed on Sep. 6, 1996 is hereby incorporated by reference.

What is claimed is:

1. A method of designing, by way of a computer, a dental prosthesis model to be attached to a part of upper and lower jaw dentitions which is to be restored, said method comprising the steps of:

displaying a dentition configuration diagram resulting from an image conversion of dentition configuration data obtained by measurement of a three-dimensional configuration of upper and lower jaw dentitions of a subject;

reading out, from a database containing pontic model data respectively indicating standard pontic models which correspond to configurations of individual teeth, pontic model data corresponding to a tooth of said part;

making, based on said read-out pontic model data, crown model data indicating a crown region;

displaying a crown model resulting from an image conversion of said crown model data so that said crown model is superimposed on said dentition configuration diagram; and deforming said crown model so that said crown model forms a desired gap with respect to pairing and adjacent teeth and a gum without interfering therewith.

2. A method according to claim 1, wherein said pontic model includes a characteristic morphology of a tooth corresponding to said pontic model and is formed by a plurality of three-dimensional curved patches combined together;

said pontic model data including morphology definition data which indicate the characteristic morphology of the tooth corresponding to said pontic model, and configuration expression data which indicate a three-dimensional configuration and constitutional position of each of said patches and are changeable upon alteration of said morphology definition data.

3. A method according to claim 1, wherein said pontic model data include deforming region definition data indicating a plurality of deforming regions divided by an interface passing through a groove of an occlusal surface in said pontic model and extending from said groove to a base surface of said pontic model; and wherein, in the step of deforming said crown model, said crown model is deformed by using said deforming region as a unit.

4. A method according to claim 1, wherein said pontic model data further include margin line data indicating a margin line corresponding to a gum line in said pontic model; and wherein, in the step of making said crown model data, crown model data indicating said crown region resulting from elimination, based on said margin line data, of a base region to be embedded in said gum from said pontic model are made.

5. A method of designing, by way of a computer, a dental prosthesis model to be attached to a plurality of parts of upper and lower jaw dentitions which are to be restored, said method comprising the steps of:

displaying a dentition configuration diagram resulting from an image conversion of dentition configuration data obtained by measurement of a three-dimensional configuration of upper and lower jaw dentitions of a subject;

reading out, from a database containing pontic model data respectively indicating standard pontic models which correspond to configurations of individual teeth, pontic model data respectively corresponding to teeth of said plurality of parts;

making, based on at least one piece of pontic model data in said read-out pontic model data, crown model data indicating a crown region;

displaying a crown model and a pontic model respectively resulting from image conversions of said crown model data and remaining pontic model data so that said crown model and pontic model are superimposed on said dentition configuration diagram;

deforming each of said crown and pontic models so that each of said crown and pontic models forms a desired gap with respect to pairing and adjacent teeth and a gum without interfering therewith; and making a bridge model by connecting said crown and pontic models to each other.

6. A method according to claim 5, wherein said pontic model includes a characteristic morphology of a tooth corresponding to said pontic model and is formed by a plurality of three-dimensional curved patches combined together;

said pontic model data including morphology definition data which indicate the characteristic morphology of the tooth corresponding to said pontic model, and configuration expression data which indicate a three-dimensional configuration and constitutional position of each of said patches and are changeable upon alteration of said morphology definition data.

7. A method according to claim 5, wherein said pontic model data include deforming region definition data indicating a plurality of deforming regions divided by an interface passing through a groove of an occlusal surface in said pontic model and extending from said groove to a base surface of said pontic model; and wherein, in the step of deforming said crown and pontic models, each of said crown and pontic models is deformed by using said deforming region as a unit.

8. A method according to claim 5, wherein said pontic model data further include margin line data indicating a margin line corresponding to a gum line in said pontic model; and wherein, in the step of making said crown model data, crown model data indicating said crown region resulting from elimination, based on said margin line data, of a base region to be embedded in said gum from said pontic model are made.

9. A computer program product for designing a dental prosthesis model, to be used in conjunction with a computer, said computer comprising a storage device for storing a database containing pontic model data respectively indicating standard pontic models corresponding to configurations of individual teeth, an input device, a display device, and a reading device for reading out information from a medium which is usable by said computer; said product comprising:

a dental prosthesis model designing program, which is readable by said computer and materialized in said medium, for designing by way of said computer, based on said pontic model data, a dental prosthesis model to be attached to a part in upper and lower jaw dentitions which is to be restored;

said dental prosthesis model designing program comprising:

a dentition configuration diagram displaying program for displaying, on said display device, a dentition configuration diagram resulting from an image conversion of dentition configuration data obtained by measurement of a three-dimensional configuration of upper and lower jaw dentitions of a subject;

a pontic model data reading program for reading out, from said database, pontic model data corresponding to a tooth of said part;

a crown model data making program for making, based on said read-out pontic model data, crown model data indicating a crown region;

a superimposition displaying program for displaying a crown model resulting from an image conversion of said crown model data so that said crown model is superimposed on said dentition configuration diagram; and a model deforming program for deforming said crown model so that said crown model forms a desired gap with respect to pairing and adjacent teeth and a gum without interfering therewith.

10. A computer program product according to claim 9, wherein said pontic model includes a characteristic morphology of a tooth corresponding to said pontic model and is formed by a plurality of three-dimensional curved patches combined together;

said pontic model data including morphology definition data which indicate the characteristic morphology of the tooth corresponding to said pontic model, and configuration expression data which indicate a three-dimensional configuration and constitutional position of each of said patches and are changeable upon alteration of said morphology definition data.

11. A computer program product according to claim 9, wherein said pontic model data include deforming region definition data indicating a plurality of deforming regions divided by an interface passing through a groove of an occlusal surface in said pontic model and extending from said groove to a base surface of said pontic model; and wherein, in the model deforming program, said crown model is deformed by using said deforming region as a unit.

12. A computer program product according to claim 9, wherein said pontic model data further include margin line data indicating a margin line corresponding to a gum line in said pontic model; and wherein, in the crown model data making program, crown model data indicating said crown region resulting from elimination, based on said margin line data, of a base region to be embedded in said gum from said pontic model are made.

13. A computer program product for designing a dental prosthesis model, to be used in conjunction with a computer, said computer comprising a storage device for storing a database containing pontic model data respectively indicating standard pontic models corresponding to configurations of individual teeth, an input device, a display device, and a reading device for reading out information from a medium which is usable by said computer; said product comprising:

a dental prosthesis model designing program, which is readable by said computer and materialized in said medium, for designing by way of said computer, based on said pontic model data, dental prosthesis models to be attached to a plurality of parts in upper and lower jaw dentitions which are to be restored;

said dental prosthesis model designing program comprising:

a dentition configuration diagram displaying program for displaying, on said display device, a dentition configuration diagram resulting from an image conversion of dentition configuration data obtained by measurement of a three-dimensional configuration of upper and lower jaw dentitions of a subject;

a pontic model data reading program for reading out, from said database, pontic model data respectively corresponding to teeth of said plurality of parts;

a crown model data making program for making, based on at least one piece of pontic model data in said read-out pontic model data, crown model data indicating a crown region;

a superimposition displaying program for displaying a crown model and a pontic model respectively resulting from image conversions of said crown model data and remaining pontic model data so that said crown model and pontic model are superimposed on said dentition configuration diagram;

a model deforming program for deforming each of said crown and pontic models so that each of said crown and pontic models forms a desired gap with respect to pairing and adjacent teeth and a gum without interfering therewith; and a model connecting program for connecting said crown and pontic models to each other so as to make a bridge model.

14. A computer program product according to claim 13, wherein said pontic model includes a characteristic morphology of a tooth corresponding to said pontic model and is formed by a plurality of three-dimensional curved patches combined together;

said pontic model data including morphology definition data which indicate the characteristic morphology of the tooth corresponding to said pontic model, and configuration expression data which indicate a three-dimensional configuration and constitutional position of each of said patches and are changeable upon alteration of said morphology definition data.

15. A computer program product according to claim 13, wherein said pontic model data include deforming region definition data indicating a plurality of deforming regions divided by an interface passing through a groove of an occlusal surface in said pontic model and extending from said groove to a base surface of said pontic model; and wherein, in the model deforming program, each of said crown and pontic models is deformed by using said deforming region as a unit.

16. A computer program product according to claim 13, wherein said pontic model data further include margin line data indicating a margin line corresponding to a gum line in said pontic model; and wherein, in the crown model data making program, crown model data indicating said crown region resulting from elimination, based on said margin line data, of a base region to be embedded in said gum from said pontic model are made.

17. A method of making a pontic model, wherein said pontic model includes a characteristic morphology of a tooth corresponding to said pontic model, comprising:

forming said characteristic morphology by combining together a plurality of three-dimensional curved patches to thereby create pontic model data, wherein said pontic model data includes morphology definition data which indicates the characteristic morphology of the tooth corresponding to said pontic model, and wherein said pontic model data also includes configuration expression data which indicates a three-dimensional configuration and constitutional position of each of said patches and are changeable upon alteration of said morphology definition data.

18. A method of deforming a pontic model that includes pontic model data, comprising:

creating deforming region definition data that indicates a plurality of deforming regions divided by an interface passing through a groove of an occlusal surface in said pontic model; and extending from said groove to a base surface of said pontic model, wherein said pontic model is deformed by using each of said deforming regions as a unit.

19. A method of making a crown model from a pontic model that includes pontic model data, the method comprising:

obtaining, from the pontic model, morphology definition data of teeth of a patient, the morphology definition data includes tooth shape data, margin line data defining a gum line of the patient, and base region data defining a base region of the teeth of the patient where the base region is located below the gum line of the patient, and creating the crown model that indicates a crown region for which a crown is to be formed, by removing the base region data of one of the teeth of the patient in which a crown is to be formed.

* * * * *

UNITED STATES PATENT AND TRADEMARK OFFICE
CERTIFICATE OF CORRECTION

PATENT NO.  : 6,049,743
DATED       : April 11, 2000
INVENTOR(S) : Masami Baba, et al.

It is certified that error appears in the above-identified patent and that said Letters Patent is hereby corrected as shown below:

Title page,
--[30   Foreign Application Priority Data

September 6, 1996 [JP] Japan.............8-236249 --.

Also [73] Assignee's Name contains a typographical error wherein "Appatus" should read -- Apparatus --.

Signed and Sealed this

Twenty-first Day of August, 2001

Attest:

*Nicholas P. Godici*

NICHOLAS P. GODICI
*Acting Director of the United States Patent and Trademark Office*

*Attesting Officer*